(12) United States Patent
Chen

(10) Patent No.: US 11,788,130 B2
(45) Date of Patent: Oct. 17, 2023

(54) COMPUTING DEVICE, STORAGE MEDIUM, AND METHOD FOR MANAGING SEQUENCING PROGRESS

(71) Applicant: Fulian Precision Electronics (Tianjin) Co., LTD., Tianjin (CN)

(72) Inventor: Jui-Chuan Chen, Neihu (TW)

(73) Assignee: Fulian Precision Electronics (Tianjin) Co., LTD., Tianjin (CN)

( * ) Notice: Subject to any disclaimer, the term of this patent is extended or adjusted under 35 U.S.C. 154(b) by 639 days.

(21) Appl. No.: 16/919,439

(22) Filed: Jul. 2, 2020

(65) Prior Publication Data

US 2021/0371916 A1    Dec. 2, 2021

(30) Foreign Application Priority Data

May 29, 2020    (CN) .......................... 202010476762.4

(51) Int. Cl.
*C12Q 1/6869*    (2018.01)
*G16B 50/30*    (2019.01)
*G16B 40/00*    (2019.01)

(52) U.S. Cl.
CPC .......... *C12Q 1/6869* (2013.01); *G16B 40/00* (2019.02); *G16B 50/30* (2019.02)

(58) Field of Classification Search
None
See application file for complete search history.

(56) References Cited

U.S. PATENT DOCUMENTS

2003/0231259 A1* 12/2003 Yui .................... H04N 21/4316
                                                              348/564

FOREIGN PATENT DOCUMENTS

| CN | 1172994 | | 2/1998 | |
| TW | 201832116 | A | 9/2018 | |
| TW | 201921376 | A | 6/2019 | |
| WO | WO-2019027767 | A1 * | 2/2019 | ........... C12Q 1/6869 |

OTHER PUBLICATIONS

Gutwin, C. Interacting with big interfaces on small screens: a comparison of fisheye, zoom, and panning techniques. Proceedings of Graphics Interface 2004, pp. 145-152. (Year: 2004).*
Reid, JG. Launching genomics into the cloud: deployment of Mercury, a next generation sequence analysis pipeline. BMC Bioinformatics 15(30): 1-11. (Year: 2014).*

* cited by examiner

*Primary Examiner* — G. Steven Vanni
*Assistant Examiner* — Robert James Kallal
(74) *Attorney, Agent, or Firm* — ScienBiziP, P.C.

(57) ABSTRACT

A method of managing sequencing progress includes obtaining a plurality of samples and controlling a gene sequencing computing device to execute gene sequencing on the plurality of samples. Once a sequencing result is obtained by sending a query instruction to the gene sequencing computing device, sequencing information of the plurality of samples is displayed when a sequencing progress of the plurality of samples is determined to be meeting the preset condition according to the sequencing result.

2 Claims, 4 Drawing Sheets

COMPUTING DEVICE, STORAGE MEDIUM, AND METHOD FOR MANAGING SEQUENCING PROGRESS

FIELD

The present disclosure relates to biotechnology technologies, in particular to a method for managing sequencing progress, a computing device, and a storage medium.

BACKGROUND

Gene sequencing technology can analyze and determine a complete sequence of genes from blood or saliva and can predict the likelihood of suffering from various diseases, and possible behavioral characteristics of individuals. Gene sequencing technology can establish genes of individual disease, assisting in the prevention and treatment of such disease in advance. Existing gene sequencing methods produce a completed gene sequence through a gene sequencer, but cannot manage a sequencing progress of multiple samples during a process of the gene sequencing.

DETAILED DESCRIPTION

In order to provide a more clear understanding of the objects, features, and advantages of the present disclosure, the same are given with reference to the drawings and specific embodiments. It should be noted that the embodiments in the present disclosure and the features in the embodiments may be combined with each other without conflict.

In the following description, numerous specific details are set forth in order to provide a full understanding of the present disclosure. The present disclosure may be practiced otherwise than as described herein. The following specific embodiments are not to limit the scope of the present disclosure.

Unless defined otherwise, all technical and scientific terms herein have the same meaning as used in the field of the art technology as generally understood. The terms used in the present disclosure are for the purposes of describing particular embodiments and are not intended to limit the present disclosure.

First Embodiment

Figure 1:
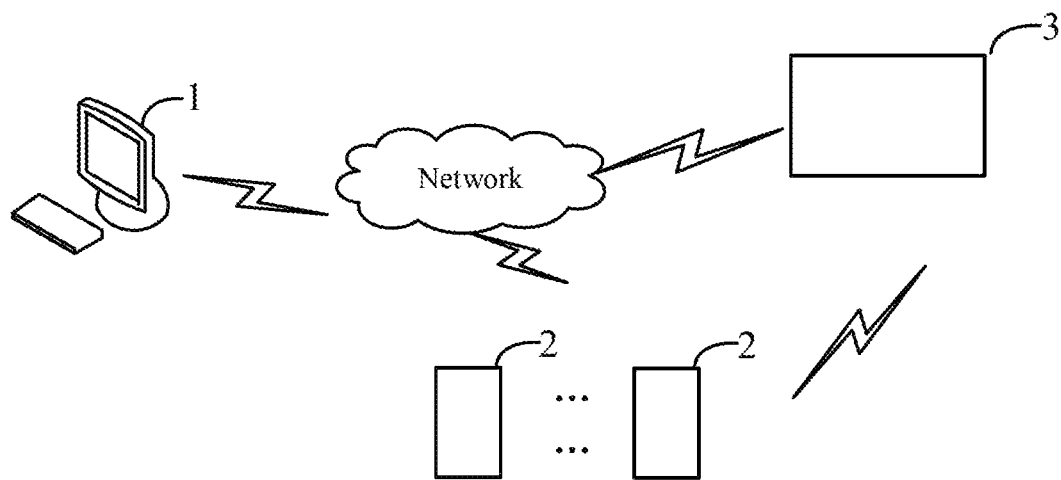
FIG. 1 is a schematic diagram of an application environment architecture of a method of managing sequencing progress provided by a first embodiment of the present disclosure.

Referring to FIG. 1, it is a schematic diagram of an application environment architecture of a method of managing a sequencing progress provided by a first embodiment of the present disclosure.

The method of managing the sequencing progress is applied to a computing device 1 in the present disclosure. The computing device 1 and at least one gene sequencing computing device 2 are in a communication connection through a network. The network may be a wired network or a wireless network, such as radio, wireless fidelity (WIFI), cellular, satellite, and broadcasting. The gene sequencing computing device 2 is used to execute gene sequencing on a plurality of samples. The computing device 1 is used to obtain the plurality of samples; control the gene sequencing computing device 2 to execute gene sequencing on the plurality of samples according to a sequencing rule; obtain a sequencing result of the plurality of samples from the gene sequencing computing device 2; determine whether a sequencing progress of the plurality of samples meets a preset condition according to the sequencing result; display sequencing information of the plurality of samples, when the sequencing progress of the plurality of samples meets the preset condition.

In other embodiments, the computing device 1 further can generate a data list according to the plurality of samples, the data list lists the plurality of samples, and the plurality of samples includes, but is not limited to, individual gene fragments, multiple sets of gene fragments that are used for comparison, and/or a combination thereof.

The computing device 1 may be an electronic device installed with software for managing the sequencing progress. The computing device 1 can be a smart phone, a tablet computer, a laptop portable computer, a desktop computer, and the like.

The gene sequencing computing device 2 may be an electronic device for executing the gene sequencing on the plurality of samples. Specifically, the gene sequencing computing device 2 receives the plurality of samples from the computing device 1; executes the gene sequencing on the plurality of samples; responds to a query instruction querying the sequencing progress of the plurality of samples which is sent by the computing device 1; and sends the sequencing result to the computing device 1. The gene sequencing computing device 2 may be a gene sequencer, a computer, a server, a cloud server, or the like.

In other embodiments, the computing device 1 further can establish a communication connection with a server 3, and the gene sequencing computing device 2 further can establish a communication connection with the server 3. The server 3 can store the plurality of samples and store the sequencing result of the plurality of samples which are sent by the gene sequencing computing device 2. The server 3 may be a computing device with a storage function, a cloud server, or the like.

Second Embodiment

Figure 2:
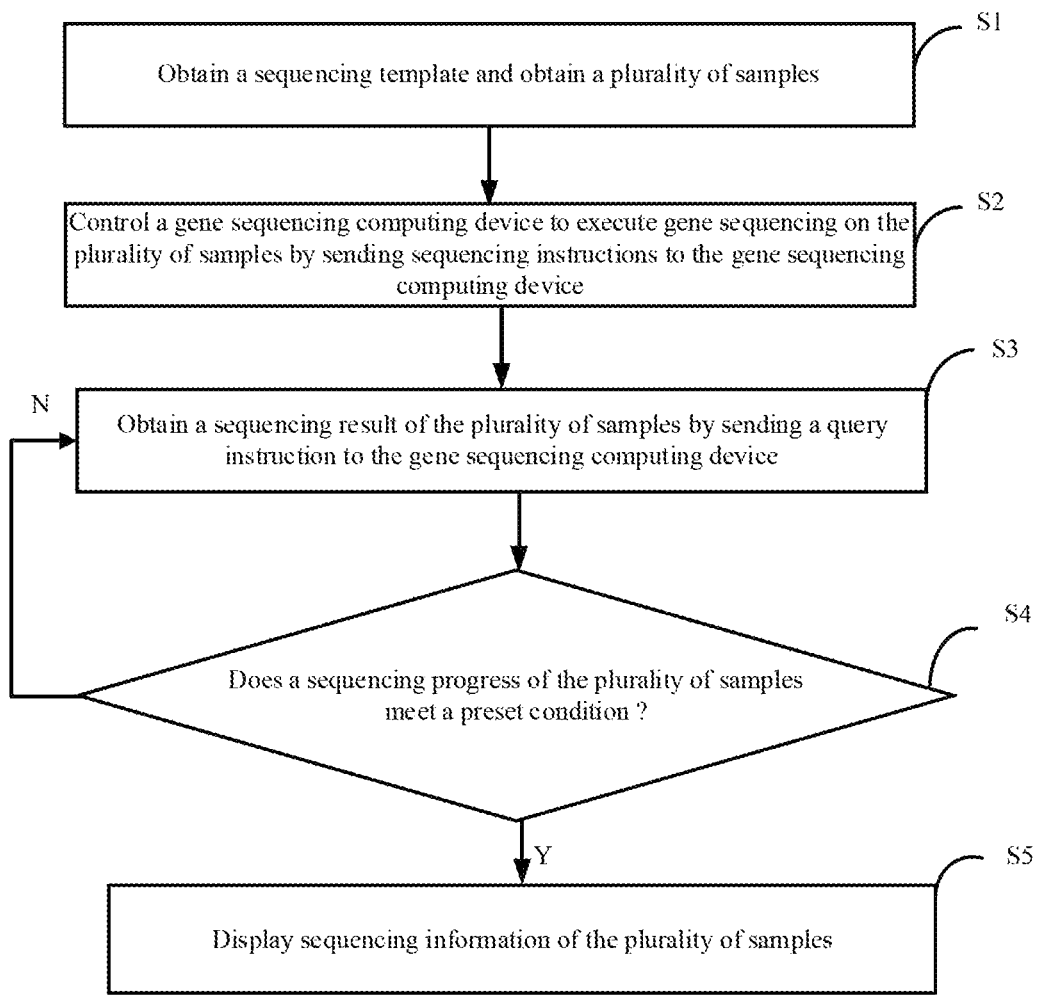
FIG. 2 is a flowchart of a method of managing sequencing progress provided by a second embodiment of the present disclosure.

FIG. 2 is a flowchart of a method of managing a sequencing progress provided by the second embodiment of the present disclosure. Referring to FIG. 2, the method is provided by way of example, as there are a variety of ways to carry out the method. The method described below can be carried out using configurations illustrated in FIG. 4, for example, and various elements of these figures are referenced in the explanation of the method. Each block is shown in FIG. 2 represents one or more processes, methods, or subroutines, carried out in the method. Furthermore, the illustrated order of blocks is illustrative only and the order of the blocks can be changed. Additional blocks can be added or fewer blocks can be utilized without departing from this disclosure. The example method can begin at block S1.

At block S1, the computing device 1 obtains a sequencing template and obtains a plurality of samples.

In one embodiment, the sample can be a set of DNA or multiple sets of DNA.

The sequencing template includes sequencing parameters. In one embodiment, the sequencing template can be one of predetermined templates. The sequencing parameters of each of the predetermined templates are different from each other. The predetermined templates may be prestored in the computing device 1 or the server 3 in advance.

In one embodiment, the sequencing parameters can include, but is not limited to, a number of detection sites, a sequencing depth.

In one embodiment, the computing device 1 obtains the plurality of samples by querying a database. The database may be stored in the server 3 or a cloud server.

In another embodiment, the computing device 1 obtains the plurality of samples in response to user input, i.e., the plurality of samples can be input by a user.

In another embodiment, the computing device 1 may obtain the plurality of samples from the gene sequencing calculation device 2.

In other embodiments, the computing device 1 determines an expense for executing gene sequencing on each of the plurality of samples, according to the sequencing parameters. In one embodiment, because more sequencing parameters result in more calculation amount of executing gene sequencing on the sample, the expense for executing gene sequencing on the sample is proportional to the sequencing parameters of the sequencing template.

Because different sequencing templates have different sequencing parameters, therefore, the expense for executing gene sequencing on each of the plurality of samples can be different when different sequencing templates are used.

In other embodiments, the computing device 1 further determines the expense for executing gene sequencing on each of the plurality of samples, according to a priority weight of each sample.

In one embodiment, the expense for executing gene sequencing on each sample is proportional to a magnitude of the priority weight of each sample. The priority weight of the sample represents a sequence of executing gene sequencing on the sample. In one embodiment, the priority weight of each sample is obtained together with each sample. In other words, the priority weight of each sample can be prestored in the database.

In another embodiment, the computing device 1 further calculates a time length of executing gene sequencing on each sample according to the sequencing parameters of the sequencing template.

In one embodiment, the calculating of the time length of executing gene sequencing on each sample according to the sequencing parameters includes: obtaining an estimated time length; recording an actual time length of one sample, wherein the actual time length of the one sample is a time length of executing gene sequencing on the one sample according to the sequencing parameters of the sequencing template; when the actual time length of the one sample is not equal to the estimated time length, setting the actual time length of the one sample as the estimated time length; and using the actual time length of the one sample as the estimated time length when executing gene sequencing on another sample according to the sequencing parameters of the sequencing template. In one embodiment, the estimated time length is pre-stored in the computing device 1 or the server 3.

At block S2, the computing device 1 controls the gene sequencing computing device 2 to execute gene sequencing on the plurality of samples by sending sequencing instructions to the gene sequencing computing device 2. The sequencing instructions include the sequencing parameters.

In one embodiment, the computing device 1 can determine an order of the plurality of samples before sending the sequencing instructions to the gene sequencing computing device 2. The computing device 1 can send the sequencing instructions to the gene sequencing computing device 2 according to the order of the plurality of samples.

In one embodiment, the computing device 1 can determine the order of the plurality of samples according to the priority weight of each of the plurality of samples.

In one embodiment, the priority weight of each of the plurality of samples together with a start time of executing gene sequencing on each of the plurality of samples are pre-stored in the computing device 1, the gene sequencing computing device 2, or the server 3.

In one embodiment, the computing device 1 determines the order of the plurality of samples by sorting the priority weight of each of the plurality of samples.

In other embodiments, the computing device 1 determines the order of the plurality of samples according to an obtaining time of obtaining each of the plurality of samples from the database.

For example, the plurality of samples includes five sets of DNAs. The priority weights of the five sets of DNAs are 0.5, 0.23, 0.15, 0.08, and 0.04, respectively. The computing device 1 sorts the five priority weights, such that the order of the five sets of DNAs is obtained.

Accordingly, the computing device 1 can first control the gene sequencing computing device 2 to execute gene sequencing on one of the five sets of DNAs of which the priority weight is the greatest, i.e., 0.5.

At block S3, the computing device 1 can obtain a sequencing result of the plurality of samples by sending a query instruction to the gene sequencing computing device 2.

In one embodiment, the computing device 1 can send the query instruction every preset time interval.

In one embodiment, the sequencing result includes a current sequencing stage, a name of a nucleotide currently being sequenced, a position of the nucleotide currently being sequenced, a result of a nucleotide sequence currently sequenced.

In one embodiment, the computing device 1 sends the query instruction to the gene sequencing computing device 2 through a data interface every preset time interval. The query instruction includes: querying the nucleotide sequence of any set of genes; or querying a sequencing result of comparison and sequencing between the nucleotide sequence of a first set of genes and the nucleotide sequence of a second set of genes.

At block S4, the computing device 1 determines whether a sequencing progress of the plurality of samples meets a preset condition according to the sequencing result.

In one embodiment, the determining of whether the sequencing progress of the plurality of samples meets the preset condition according to the sequencing result includes:

searching predetermined feature information from the sequencing result, wherein the predetermined feature information indicates the sequencing stage;

determining that the sequencing progress of the plurality of samples meets the preset condition when the sequencing result includes the predetermined feature information.

For example, the gene sequencing includes three sequencing stages. A first sequencing stage of the three sequencing stages is to compare gene positions, a second sequencing stage of the three sequencing stages is to mark repeat positions and sort positions, and a third sequencing stage of the three sequencing stages is to identify nucleobases. The feature information of the first sequencing stage is a file with an extension name "BAM", because the file with the extension name "BAM" is output in the first sequencing stage. Accordingly, when the file with the extension name "BAM" is obtained from the sequencing result, the computing device 1 can determine that the first sequencing stage is finished.

In other embodiments, the determining of whether the sequencing progress of the plurality of samples meets the preset condition according to the sequencing result includes:

obtaining a number of nucleotide sequences that have been sequenced from the sequencing result;

comparing the number of nucleotide sequences that have been sequenced with a preset threshold; and determining that the sequencing progress of the plurality of samples meets the preset condition when the number of nucleotide sequences that have been sequenced is greater than the preset threshold.

At block S5, when the sequencing progress of the plurality of samples meets the preset condition, the computing device 1 displays sequencing information of the plurality of samples.

In one embodiment, the displaying of the sequencing information of the plurality of samples includes:

obtaining a display mode, wherein the display mode can include, but is not limited to, a sequencing status, a progress bar, and a progress value of the progress bar; and displaying the sequencing information of the plurality of samples according to the display mode.

In one embodiment, the sequencing status may be a status of waiting for sequencing, a status of being sequence, or a status of sequencing completed. In one embodiment, the progress value represents a percentage of the gene sequencing that has been completed. The progress bar may include a number of preset patterns to indicate the percentage of the gene sequencing that has been completed. For example, the preset pattern is a rectangle. The progress bar includes five rectangles when the gene sequencing has been fully completed. The progress bar includes three rectangles when 60% of the gene sequencing has been fully completed. In one embodiment, the computing device 1 can preset the display mode in response to user input. In one embodiment, the display mode may be prestored in a storage device of the computing device 1, or a cloud server.

In at least one embodiment, the displaying of the sequencing information of the plurality of samples according to the display mode includes (1)-(4):

(1) acquiring an area of a display area of a display device of the computing device 1.

In a first embodiment, the acquiring of the area of the display area includes: acquiring a preset number of mark positions in the display area, and calculating the area of the display area according to the mark positions.

In one embodiment, the preset number equals four. Each of the four mark positions represents a position of one of four corners of the display area. The computing device 1 can calculate the area of the display area according to a coordinate of each of the four mark positions.

In one embodiment, the acquiring of the preset number of mark positions includes: determining a target pixel point in the display area, wherein the target pixel point is a pixel point located in a middle of the display area; determining whether there is a pixel point adjacent to the target pixel point in each of four directions of the target pixel point, wherein the four directions includes an upwards direction, a downwards direction, a leftwards direction, and a rightwards direction; when there is pixel point adjacent to the target pixel point in each of the four directions, moving a position of the target pixel point by one pixel in a first direction of the four directions; when there is no pixel point adjacent to the target pixel point in the first direction, moving a position of the target pixel point by one pixel in a second direction of the four directions, wherein the second direction is adjacent to the first direction; when there is no pixel point adjacent to the target pixel point in two of the four directions, setting a current position of the target pixel point as the marking position.

In a second embodiment, the acquiring of the area of the display area includes: obtaining an image of the display area of display device; and counting a number of pixels included in the image; setting the number of the pixels as the area of the display area.

(2) comparing the area with a preset threshold.

(3) displaying the sequencing information of the plurality of samples in a first mode when the area is greater than the preset threshold.

(4) displaying the sequencing information of the plurality of samples in a second mode when the area is less than or equal to the preset threshold.

In one embodiment, the sequencing information of the plurality of samples includes, but is not limited to, the sequencing status of each sample, the progress bar and the progress value of the progress bar corresponding each sample.

In one embodiment, the sequencing information displayed on the display area in the first mode is more than the sequencing information displayed on the display area in the second mode. In other words, the display mode can be the first mode or the second mode.

For example, when the sequencing information of the plurality of samples is displayed in the first mode, the sequencing status of each sample, the progress bar, and the progress value of the progress bar corresponding to each sample are displayed in the display area. When the sequencing information of the plurality of samples is displayed in the second mode, only the sequencing status of each sample, and the progress bar corresponding to each sample are displayed in the display area.

In other embodiments, the computing device 1 further acquires the sequencing result of the plurality of samples and stores the sequencing result of the plurality of samples in a preset database such as a local server or a cloud server.

Figure 3:
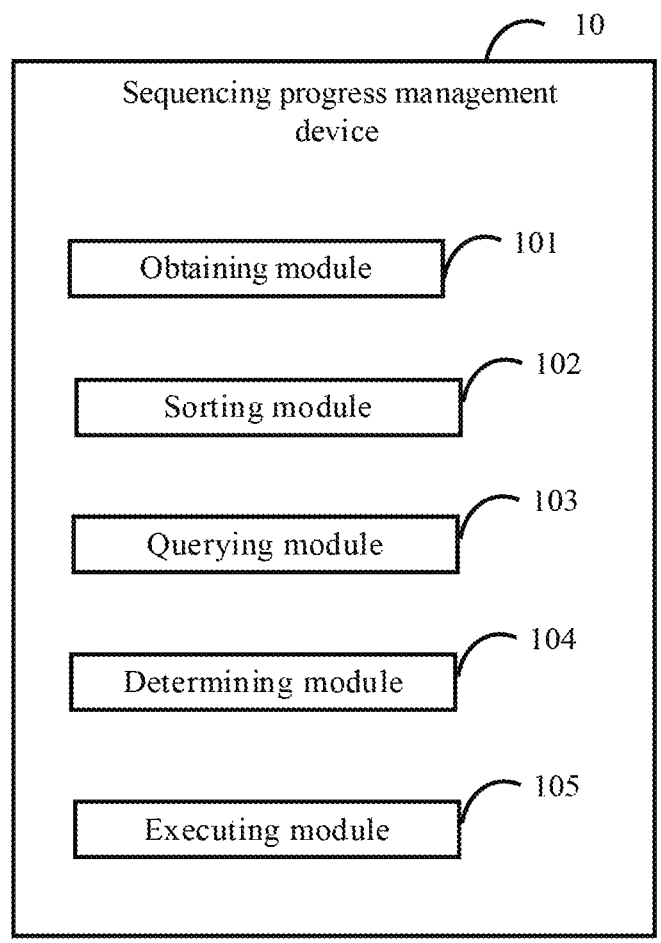
FIG. 3 is a block diagram of a sequencing progress management device provided by a third embodiment of the present disclosure.
Figure 4:
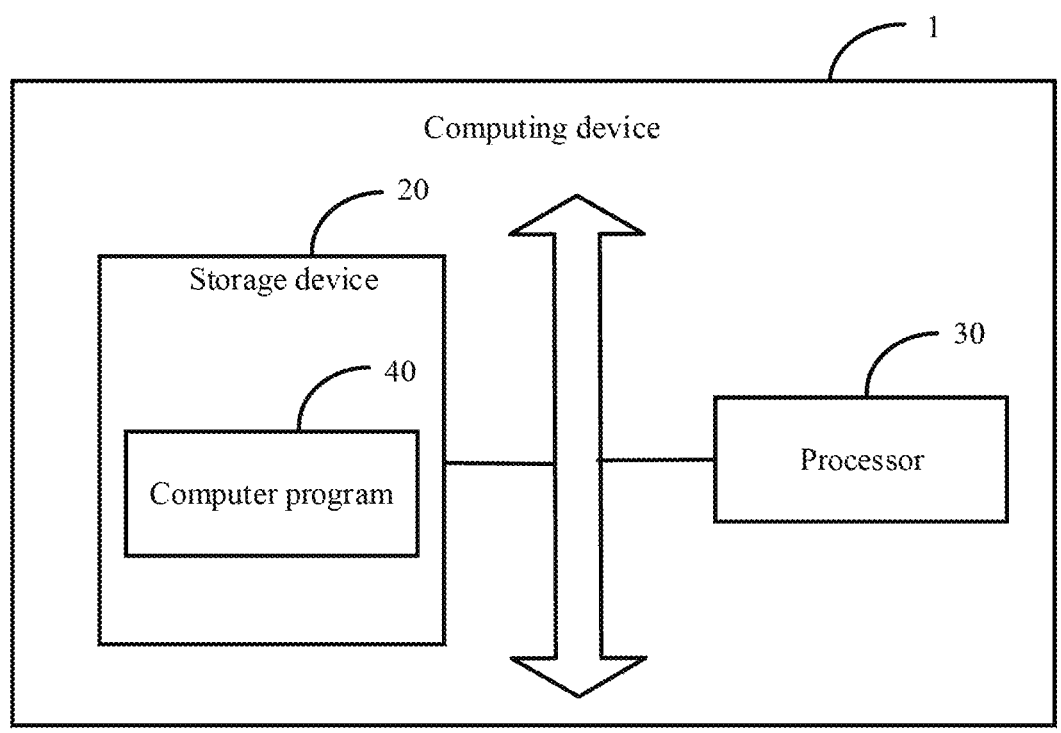
FIG. 4 is a schematic diagram of a computing device provided by a fourth embodiment of the present disclosure.

The above-mentioned FIG. 2 details the method of managing the sequencing progress of the present disclosure. With reference to FIGS. 3-4, the following introduces functional modules of software implementing the method of managing the sequencing progress and the hardware implementing the method of managing the sequencing progress.

It should be understood that the embodiments are for illustrative purposes only and are not limited by this structure in the scope of the present disclosure.

Third Embodiment

FIG. 3 shows a block diagram of an embodiment of a sequencing progress management device.

In some embodiments, the sequencing progress management device 10 runs in a computing device. The computing device is connected to multiple gene sequencing computing devices through a network. The sequencing progress management device 10 may include a plurality of modules. The plurality of modules can comprise computerized instructions in a form of one or more computer-readable programs that can be stored in a non-transitory computer-readable medium (e.g., a storage device 20 of the computing device 1 in FIG. 4), and executed by at least one processor (e.g., a processor 30 in FIG. 4) of the computing device to implement a function of managing sequencing progress (described in detail in FIG. 2).

In at least one embodiment, the sequencing progress management device 10 may include a plurality of modules. The plurality of modules may include, but is not limited to, an obtaining module 101, a sorting module 102, a querying module 103, a determining module 104, and an executing module 105. The modules 101-105 can comprise computerized instructions in the form of one or more computer-readable programs that can be stored in the non-transitory computer-readable medium (e.g., the storage device 20 of the computing device 1), and executed by the at least one processor (e.g., the processor 30) of the computing device to implement the function of managing sequencing progress.

The obtaining module 101 obtains a sequencing template and obtains a plurality of samples.

In one embodiment, the sample can be a set of DNA or multiple sets of DNA.

The sequencing template includes sequencing parameters. In one embodiment, the sequencing template can be one of predetermined templates. The sequencing parameters of each of the predetermined templates are different from each other. The predetermined templates may be prestored in the computing device 1 or the server 3 in advance.

In one embodiment, the sequencing parameters can include, but is not limited to, a number of detection sites, a sequencing depth.

In one embodiment, the obtaining module 101 obtains the plurality of samples by querying a database. The database may be stored in the server 3 or a cloud server.

In another embodiment, the obtaining module 101 obtains the plurality of samples in response to user input, i.e., the plurality of samples can be input by a user.

In another embodiment, the obtaining module 101 may obtain the plurality of samples from the gene sequencing calculation device 2.

In another embodiment, the obtaining module 101 determines an expense for executing gene sequencing on each of the plurality of samples, according to the sequencing parameters. In one embodiment, because more sequencing parameters result in more calculation amount of executing gene sequencing on each of the plurality of samples, the expense for executing gene sequencing on each of the plurality of samples is proportional to the sequencing parameters of the sequencing template.

Because different sequencing templates have different sequencing parameters, therefore, the expense for executing gene sequencing on each of the plurality of samples can be different when different sequencing templates are used.

In other embodiments, the obtaining module 101 further determines the expense for executing gene sequencing on each of the plurality of samples, according to a priority weight of each sample.

In one embodiment, the expense for executing gene sequencing on each sample is proportional to a magnitude of the priority weight of each sample. The priority weight of the sample represents a sequence of executing gene sequencing on the sample.

In another embodiment, the obtaining module 101 further calculates a time length of executing gene sequencing on each sample according to the sequencing parameters of the sequencing template.

In one embodiment, the calculating of the time length of executing gene sequencing on each sample according to the sequencing parameters includes: obtaining an estimated time length; recording an actual time length of one sample, wherein the actual time length of the one sample is a time length of executing gene sequencing on the one sample according to the sequencing parameters of the sequencing template; when the actual time length of the one sample is not equal to the estimated time length, setting the actual time length of the one sample as the estimated time length; and using the actual time length of the one sample as the estimated time length when executing gene sequencing on another sample according to the sequencing parameters of the sequencing template. In one embodiment, the estimated time length is pre-stored in the computing device 1 or the server 3.

The sorting module 102 controls the gene sequencing computing device 2 to execute gene sequencing on the plurality of samples by sending sequencing instructions to the gene sequencing computing device 2. The sequencing instructions include the sequencing parameters.

In one embodiment, the sorting module 102 can determine the order of the plurality of samples according to the priority weight of each of the plurality of samples.

In one embodiment, the sorting module 102 can determine the order of the plurality of samples according to the priority weight of each of the plurality of samples.

In one embodiment, the priority weight of each of the plurality of samples together with a start time of executing gene sequencing on each of the plurality of samples are pre-stored in the computing device 1, the gene sequencing computing device 2, or the server 3.

In one embodiment, the sorting module 102 determines the order of the plurality of samples by sorting the priority weight of each of the plurality of samples.

In other embodiments, the sorting module 102 determines the order of the plurality of samples according to an obtaining time of obtaining each of the plurality of samples from the database.

For example, the plurality of samples includes five sets of DNAs. The priority weights of the five sets of DNAs are 0.5, 0.23, 0.15, 0.08, and 0.04, respectively. The sorting module 102 sorts the five priority weights, such that the order of the five sets of DNAs is obtained.

Accordingly, the sorting module 102 can first control the gene sequencing computing device 2 to execute gene sequencing on one of the five sets of DNAs of which the priority weight is the greatest, i.e., 0.5.

The querying module 103 can obtain a sequencing result of the plurality of samples by sending a query instruction to the gene sequencing computing device 2.

In one embodiment, the querying module 103 can send the query instruction every preset time interval.

In one embodiment, the sequencing result includes a current sequencing stage, a name of a nucleotide currently being sequenced, a position of the nucleotide currently being sequenced, a result of a nucleotide sequence currently sequenced.

In one embodiment, the querying module 103 sends the query instruction to the gene sequencing computing device 2 through a data interface every preset time interval. The query instruction includes: querying the nucleotide sequence of any set of genes; or querying a sequencing result of comparison and sequencing between the nucleotide sequence of a first set of genes and the nucleotide sequence of a second set of genes.

The determining module 104 determines whether a sequencing progress of the plurality of samples meets a preset condition according to the sequencing result.

In one embodiment, the determining of whether the sequencing progress of the plurality of samples meets the preset condition according to the sequencing result includes:

searching predetermined feature information from the sequencing result, wherein the predetermined feature information indicates the sequencing stage;

determining that the sequencing progress of the plurality of samples meets the preset condition when the sequencing result includes the predetermined feature information.

For example, the gene sequencing includes three sequencing stages. A first sequencing stage of the three sequencing stages is to compare gene positions, a second sequencing stage of the three sequencing stages is to mark repeat positions and sort positions, and a third sequencing stage of the three sequencing stages is to identify nucleobases. The feature information of the first sequencing stage is a file with an extension name "BAM", because the file with the extension name "BAM" is output in the first sequencing stage. Accordingly, when the file with the extension name "BAM" is obtained from the sequencing result, the determining module 104 can determine that the first sequencing stage is finished.

In other embodiments, the determining of whether the sequencing progress of the plurality of samples meets the preset condition according to the sequencing result includes:

obtaining a number of nucleotide sequences that have been sequenced from the sequencing result;

comparing the number of nucleotide sequences that have been sequenced with a preset threshold; and determining that the sequencing progress of the plurality of samples meets the preset condition when the number of nucleotide sequences that have been sequenced is greater than the preset threshold.

When the sequencing progress of the plurality of samples meets the preset condition, the executing module 105 displays sequencing information of the plurality of samples.

In one embodiment, the displaying of the sequencing information of the plurality of samples includes:

obtaining a display mode, wherein the display mode can include, but is not limited to, a sequencing status, a progress bar, and a progress value of the progress bar; and displaying the sequencing information of the plurality of samples according to the display mode.

In one embodiment, the sequencing status may be a status of waiting for sequencing, a status of being sequence, or a status of sequencing completed. In one embodiment, the progress value represents a percentage of the gene sequencing that has been completed. The progress bar may include a number of preset patterns to indicate the percentage of the gene sequencing that has been completed. For example, the preset pattern is a rectangle. The progress bar includes five rectangles when the gene sequencing has been fully completed. The progress bar includes three rectangles when 60% of the gene sequencing has been fully completed. In one embodiment, the executing module 105 can preset the display mode in response to user input. In one embodiment, the display mode may be prestored in a storage device of the computing device 1, or a cloud server.

In at least one embodiment, the displaying of the sequencing information of the plurality of samples according to the display mode includes:

(1) acquiring an area of a display area of a display device of the computing device 1.

In a first embodiment, the acquiring of the area of the display area includes: acquiring a preset number of mark positions in the display area and calculating the area of the display area according to the mark positions.

In one embodiment, the preset number equals four. Each of the four mark positions represents a position of one of four corners of the display area. The executing module 105 can calculate the area of the display area according to a coordinate of each of the four mark positions.

In one embodiment, the acquiring of the preset number of mark positions includes: determining a target pixel point in the display area, wherein the target pixel point is a pixel point located in a middle of the display area; determining whether there is a pixel point adjacent to the target pixel point in each of four directions of the target pixel point, wherein the four directions includes an upwards direction, a downwards direction, a leftwards direction, and a rightwards direction; when there is pixel point adjacent to the target pixel point in each of the four directions, moving a position of the target pixel point by one pixel in a first direction of the four directions; when there is no pixel point adjacent to the target pixel point in the first direction, moving a position of the target pixel point by one pixel in a second direction of the four directions, wherein the second direction is adjacent to the first direction; when there is no pixel point adjacent to the target pixel point in two of the four directions, setting a current position of the target pixel point as the marking position.

In a second embodiment, the acquiring of the area of the display area includes: obtaining an image of the display area of the display device; counting a number of pixels included in the image; and setting the number of the pixels as the area of the display area.

(2) comparing the area with a preset threshold.

(3) displaying the sequencing information of the plurality of samples in a first mode when the area is greater than the preset threshold.

(4) displaying the sequencing information of the plurality of samples in a second mode when the area is less than or equal to the preset threshold.

In one embodiment, the sequencing information of the plurality of samples includes, but is not limited to, the sequencing status of each sample, the progress bar and the progress value of the progress bar corresponding to each sample.

In one embodiment, the sequencing information displayed on the display area in the first mode is more than the sequencing information displayed on the display area in the second mode. In other words, the display mode can be the first mode or the second mode.

For example, when the sequencing information of the plurality of samples is displayed in the first mode, the sequencing status of each sample, the progress bar, and the progress value of the progress bar corresponding to each sample are displayed in the display area. When the sequencing information of the plurality of samples is displayed in the second mode, only the sequencing status of each sample, and the progress bar corresponding to each sample are displayed in the display area.

In other embodiments, the executing module 105 further acquires the sequencing result of the plurality of samples and stores the sequencing result of the plurality of samples in a preset database such as a local server or a cloud server.

FIG. 4 shows a schematic block diagram of one embodiment of a computing device 1.

The computing device 1 includes a storage device 20, a processor 30, and a computer program 40 stored in the storage device 20 and executable by the processor 30. The computer program 40 can be a program for managing sequencing progress. When the processor 30 executes the computer program 40, the method for managing sequencing progress described in FIG. 2 is achieved. Alternatively, when the processor 30 executes the computer program 40, the functions of each module in the embodiment of the sequencing progress management device described above, such as the modules 101-105 in FIG. 3, are implemented.

Exemplarily, the computer program 40 may be divided into one or more modules/units, and the one or more modules/units are stored in the storage device 20 and executed by the processor 30 to complete this disclosure. The one or more modules/units may be a series of computer program instruction segments capable of performing specific functions, and the instruction segments are used to describe the execution process of the computer program 40 in the computing device 1. For example, the computer program 40 may be divided into an obtaining module 101, a sorting module 102, a querying module 103, a determining module 104, and an executing module 105 in FIG. 3.

The computing device 1 may be a computing device such as a desktop computer, a notebook, a palmtop computer, and a cloud server. A person skilled in the art may understand that the schematic diagram is only an example of the computing device 1 and does not constitute a limitation on the computing device 1, and may include more or fewer components than the illustration, or a combination of certain components, or different components, for example, the computing device 1 may also include input and output devices, network access devices, buses, and the like. In at least one embodiment, the processor 30 may be a central processing unit (CPU), or other general-purpose processors, digital signal processors DSP, application specific integrated circuits ASIC, Ready-made programmable gate array (Field-Programmable Gate Array, FPGA) or other programmable logic devices, discrete gate or transistor logic devices, discrete hardware components, etc. The general-purpose processor may be a microprocessor or the processor 30 may also be any conventional processor, etc. The processor 30 is a control center of the computing device 1 and uses various interfaces and lines to connect various parts of the computing device 1.

In at least one embodiment, the storage device 20 may be used to store the computer program 40 and/or modules/units, and the processor 30 executes or executes the computer programs and/or modules/units stored in the storage device 20 and calls up data stored in the storage device 20 to realize various functions of the computing device 1. The storage device 20 may include a first area for storing programs and a second area for storing data, wherein the first area may store an operating system, application programs required by at least one function (such as a sound playback function, image playback function), and so on. The second area may store data (such as audio data, address book) created according to the use of the computing device 1. In addition, the storage device 20 may include random access memory, and may also include non-volatile memory, such as a hard disk, a memory, a plug-in hard disk, a Smart Media Card SMC, and a secure digital (SD) Card, a flash card, at least one disk storage device, flash memory device, or another non-volatile solid-state storage device.

If the module/unit integrated into the computing device 1 is implemented in the form of a software functional module and sold or used as an independent product, it may be stored in a computer-readable storage medium. Based on this understanding, the present disclosure can implement all or part of the processes in the methods of the above embodiments and can also be completed by a relevant hardware of computer program instructing. The computer program can be stored in a computer-readable storage medium. When the computer program is executed by the processor, the steps of the foregoing method embodiments may be implemented. Wherein, the computer program includes computer program codes, and the computer program codes may be in the form of source codes, object codes, executable file, or some intermediate form. The computer readable medium may include: any entity or device capable of carrying the computer program codes, a recording medium, a U disk, a mobile hard disk, a magnetic disk, an optical disk, a computer memory, a read-only memory (ROM, Read-Only Memory), Random Access Memory (RAM, Random Access Memory), electrical carrier signals, telecommunications signals, and software distribution media, etc. It should be noted that the content contained in the computer-readable medium can be appropriately increased or decreased according to the requirements of legislation and patent practice in jurisdictions. For example, in some jurisdictions, according to legislation and patent practice, computer-readable media does not include electrical carrier signals and telecommunications signals.

In the several embodiments provided by the present disclosure, it should be understood that the disclosed computing device and method may be implemented in other ways. For example, the computing device embodiments described above are only schematic. For example, the division of the unit is only a logical function division, and there may be other division manners in actual implementation.

In addition, the functional units in the embodiments of the present disclosure may be integrated in the same processing unit, or each unit may exist alone physically, or two or more units may be integrated in the same unit. The above integrated unit can be implemented in the form of hardware, or in the form of hardware plus software function modules.

It will be apparent to those skilled in the art that the present disclosure is not limited to the details of the above exemplary embodiments, and that the present disclosure can be implemented in other specific forms without departing from the spirit or basic characteristics of the present disclosure. Therefore, no matter from which point of view, the embodiments should be regarded as exemplary and non-limiting, the scope of the present disclosure is defined by the appended claims rather than the above description, and is therefore intended to fall within the claims All changes within the meaning and scope of the equivalent requirements are included in the present disclosure. Any reference signs in the claims should not be considered as limiting the claims involved. In addition, it is clear that the word "include" does not exclude other units or steps, and the singular does not exclude the plural. Multiple units or computing devices stated in the computing device claims may also be implemented by the same unit or computing device through software or hardware. The first and second words are used to indicate names, but do not indicate any particular order.

The above description is only embodiments of the present disclosure and is not intended to limit the present disclosure, and various modifications and changes can be made to the present disclosure. Any modifications, equivalent substitutions, improvements, etc. made within the spirit and scope of the present disclosure are intended to be included within the scope of the present disclosure.

What is claimed is:

1. A method of managing sequencing progress applied to a computing device, the method comprising:
    obtaining a sequencing template and obtaining a plurality of samples, wherein the sequencing template comprises sequencing parameters;
    controlling a gene sequencing computing device to execute gene sequencing on the plurality of samples by sending sequencing instructions to the gene sequencing computing device, wherein the sequencing instruction comprises the sequencing parameters;
    obtaining a sequencing result of the plurality of samples by sending a query instruction to the gene sequencing computing device;
    determining whether a sequencing progress of the plurality of samples meets a preset condition according to the sequencing result; and
    displaying sequencing information of the plurality of samples on a display device of the computing device when the sequencing progress of the plurality of samples meets the preset condition, comprising: acquiring an area of a display area of the display device; comparing the area with a preset threshold; displaying the sequencing information in a first mode when the area is greater than the preset threshold; and displaying the sequencing information in a second mode when the area is less than or equal to the preset threshold, more of the sequencing information being displayed on the display area in the first mode than the second mode;
    wherein the acquiring of the area of the display area comprises: obtaining an image of the display area; counting a number of pixels comprised in the image; and setting the number of the pixels as the area of the display area.

2. A computing device comprising:
    a storage device;
    at least one processor; and
    the storage device storing one or more programs, which when executed by the at least one processor, cause the at least one processor to:
    obtain a sequencing template and obtain a plurality of samples, wherein the sequencing template comprises sequencing parameters;
    control a gene sequencing computing device to execute gene sequencing on the plurality of samples by sending sequencing instructions to the gene sequencing computing device, wherein the sequencing instruction comprises the sequencing parameters;
    obtain a sequencing result of the plurality of samples by sending a query instruction to the gene sequencing computing device;
    determine whether a sequencing progress of the plurality of samples meets a preset condition according to the sequencing result; and
    display sequencing information of the plurality of samples on a display device of the computing device when the sequencing progress of the plurality of samples meets the preset condition, comprising: acquiring an area of a display area of the display device; comparing the area with a preset threshold; displaying the sequencing information in a first mode when the area is greater than the preset threshold; and displaying the sequencing information in a second mode when the area is less than or equal to the preset threshold, more of the sequencing information being displayed on the display area in the first mode than the second mode;
    wherein the acquiring of the area of the display area comprises: obtaining an image of the display area; counting a number of pixels comprised in the image; and setting the number of the pixels as the area of the display area.

* * * * *